United States Patent [19]

Zabotto et al.

[11] Patent Number: 5,154,854
[45] Date of Patent: * Oct. 13, 1992

[54] PROCESS FOR THE PREPARATION OF STABLE DISPERSIONS OF AT LEAST ONE WATER-IMMISCIBLE LIQUID PHASE IN AN AQUEOUS PHASE

[75] Inventors: Arlette Zabotto, Paris; Jacqueline Griat, Ablon; Rose-Marie J. Handjani, Paris; Guy G. Vanlerberghe, Villevaude; Alain J. Ribier, Paris, all of France

[73] Assignee: L'Oreal, Paris, France

[*] Notice: The portion of the term of this patent subsequent to Oct. 8, 2008 has been disclaimed.

[21] Appl. No.: 664,786

[22] Filed: Mar. 5, 1991

Related U.S. Application Data

[63] Continuation of Ser. No. 167,994, Mar. 14, 1988, Pat. No. 5,055,228, which is a continuation-in-part of Ser. No. 900,772, Aug. 26, 1986, abandoned, which is a continuation of Ser. No. 279,518, Jul. 1, 1981, abandoned.

[30] Foreign Application Priority Data

Jul. 1, 1980 [FR] France ................................ 80 14657
Sep. 24, 1980 [FR] France ................................ 80 20499

[51] Int. Cl.$^5$ .............................................. B01J 13/00
[52] U.S. Cl. .................................. 252/312; 252/315.2; 252/315.6; 264/4.1
[58] Field of Search .................. 252/312, 315.1, 315.6; 264/4.1

[56] References Cited

U.S. PATENT DOCUMENTS

| | | | |
|---|---|---|---|
| 3,957,971 | 5/1976 | Oleniacz | 424/358 |
| 4,217,344 | 8/1980 | Vanlerberghe | 252/318 |
| 4,224,179 | 9/1980 | Schneider | 252/315.2 |
| 4,776,976 | 10/1988 | Nakamura | 252/312 |
| 4,776,991 | 10/1988 | Farmer | 264/4.3 |
| 4,789,633 | 12/1988 | Huange | 264/4.3 |

FOREIGN PATENT DOCUMENTS

| | | |
|---|---|---|
| 2221122 | 4/1973 | France . |
| 2278321 | 7/1973 | France . |
| 2298318 | 10/1973 | France . |
| 2315991 | 10/1973 | France . |
| 2408387 | 11/1976 | France . |

Primary Examiner—C. Warren Ivy
Assistant Examiner—Catherine Scalzo
Attorney, Agent, or Firm—Cushman, Darby & Cushman

[57] ABSTRACT

A process for the preparation of a stable emulsion of at least one water-immiscible liquid phase L in an aqueous phase D is described which comprises mixing the liquid phase or phases L with a dispersion of spheres in an aqueous phase D, the spheres having an average diameter of 0.025 to 5 microns and consisting of substantially concentric lipid laminae encapsulating an aqueous phase E between them, the lipid or lipids constituting the laminae being ionic or nonionic amphiphilic substances capable of forming a lamellar phase in water, and subjecting the whole to mechanical agitation so as to disperse the phase (or phases) L in the phase D in the form of droplets having an average diameter of 0.1 micron to a few microns.

2 Claims, No Drawings

PROCESS FOR THE PREPARATION OF STABLE DISPERSIONS OF AT LEAST ONE WATER-IMMISCIBLE LIQUID PHASE IN AN AQUEOUS PHASE

This is a continuation of application No. 17/167,994, filed Mar. 14, 1988, now U.S. Pat. No. 5,055,228 which is a continuation-in-part of Ser. No. 06/900,772 filed Aug. 26, 1986, now abandoned, which is a continuation of Ser. No. 06/279,518, filed Jul. 1, 1981, now abandoned.

The present invention relates to a process for the preparation of stable dispersions of at least one water-immiscible liquid phase in an aqueous phase.

It is known that if a water-immiscible liquid phase is mixed into an aqueous phase by mechanical agitation, for example by means of an ultra-disperser, the stability of the dispersion most frequently requires the addition of an emulsifying agent, the molecules of which are adsorbed onto the surface of the droplets of the water-immiscible liquid phase to form a kind of continuous membrane which prevents direct contact between two adjacent droplets, for example during shock. The droplets of water-immiscible liquid phase can contain substances soluble in an organic medium. However, it can be desirable to produce dispersions which contain, in micro-reservoirs similar to those formed by the above-mentioned droplets, water-soluble substances capable of acting in coordination with that of the liposoluble substances contained in the droplets.

It is furthermore known to produce aqueous dispersions of small lipid spheres (see French Patent 2,221,122 and U.S. Pat. No. 4,217,344). These small lipid spheres consist of several substantially concentric lipid laminae separated from one another by layers of aqueous phase; these small spheres can be used to encapsulate water-soluble active substances in the aqueous compartments between the lipid layers.

According to the present invention, it has been found that it is possible to stabilize droplets of water-immiscible liquid by the presence, in the same dispersion, of such small lipid spheres. This observation will be particularly surprising to those skilled in the art because, although it is possible to imagine that the amphiphilic lipids constituting the small spheres could act as an emulsifier by being adsorbed onto the surface of the oil droplets, one would nevertheless expect that such stabilization of the oil droplets would cause the destruction of the concentric laminae of the small spheres. On the contrary, it has been found that these small spheres stabilize the droplets of immiscible liquid in the overall dispersion, and that, conversely, the droplets of water-immiscible liquid contribute to the stability of the small lipid spheres. The dispersions thus obtained possess a remarkable stability under normal storage conditions; the small spheres retain their integrity, which is all the more surprising because the organic liquids generally have a solvent action towards the amphiphilic lipids of the small spheres.

The dispersions obtained by the process according to the invention thus consist of a continuous aqueous phase in which droplets of immiscible liquid, on the one hand, and small spheres of concentric lipid laminae, on the other hand, are held in suspension; it is believed that the droplets are held in suspension by the small spheres adsorbed on their surface. The formation and the stability of such dispersions of course depend firstly on the nature of the immiscible liquid to be dispersed, secondly on the nature of the amphiphilic substances forming the walls of the small spheres, and lastly on the conditions under which the process is carried out.

The present invention provides a process for the preparation of a stable dispersion consisting of droplets of at least one water-immiscible liquid phase L dispersed in a continuous aqueous phase D. The spheres have an average diameter of 0.025 to 5 microns and consist of substantially concentric lipid laminae encapsulating an aqueous phase E between them. The lipids constituting the laminae are ionic or nonionic amphiphilic substances which are capable of forming a lamellar phase in water. This dispersion and the liquid phase (or phases) L are mixed, and the whole is subjected to mechanical agitation in order to disperse the phase (or phases) L in the phase D in the form of said droplets having an average diameter of 0.1 micron to a few microns. The aqueous phase D contains no amphiphilic substance other than the amphiphilic substance constituting the laminae of the said spheres.

In a preferred embodiment, in order to mix the dispersion of small spheres with the liquid phase (or phases) L, the said liquid phase (or phases) L are added to the dispersion of small spheres; each water-immiscible liquid phase L should consist of one or more compounds having a molecular volume of at least 200 $cm^3/mol$; preferably, a single liquid phase L is dispersed in the phase D.

Any known process can be used to produce the dispersion of the small lipid spheres in the aqueous phase D. For example, it is possible to dissolve the lipids in a volatile solvent, form a thin film of lipids on the walls of a flask by evaporating off the solvent, introduce the aqueous phase E to be encapsulated into the said flask, and agitate the mixture mechanically until the dispersion of small spheres of the desired size is obtained; in this case, the aqueous phases D and E are necessarily identical. It is preferred to use the process described in U.S. Pat. No. 4,217,344 the disclosure of which is hereby incorporated by reference. This process consists in forming a plane lamellar phase by introducing the aqueous phase E to be encapsulated into the liquid lipids, at a temperature slightly above the melting point of the lipids, subsequently adding, to the lamellar phase obtained, an aqueous dispersion phase D, which may or may not be identical to the aqueous phase E, and in vigorously agitating, for example mechanically, in order to convert the plane lamellar phase into a dispersion, in the aqueous phase D, of small lipid spheres encapsulating the aqueous phase E. Depending on the means used to produce the dispersion e.g. ultra-disperser and/or ultrasound, and depending on the agitation time, e.g. from 15 minutes to a few hours, small spheres having an average diameter from 0.025 to 5 microns are generally obtained.

The dispersion of the water-immiscible liquid phase (or phases) L is advantageously produced with the aid of an ultra-disperser, at a temperature in the region of ambient temperature, which represents a significant advantage from the economic point of view, for the stability of the constituents of the composition, in particular if they are volatile or oxidizable, and for safety. The average diameter of the droplets of liquid L obtained is from 0.1 to a few microns.

The lipids used for the preparation of the small spheres are ionic or nonionic amphiphilic substances of natural or synthetic origin, which contain, per molecule, one or more long hydrocarbon chains or one or more hydrophilic groups, in general hydroxyl, ether, carboxyl, phosphate, amine or ammonium groups.

Amongst the ionic amphiphilic substances, it is preferred to use natural phospholipids, for example egg lecithin, soya lecithin or sphingomyelin, synthetic phospholipids, for example dipalmitoyl-phosphatidyl-choline or hydrogenated lecithin, and cationic or quaternary compounds, for example dialkyldimethylammonium chloride or bromide such as didodecyl- or distearyldimethylammonium chloride or bromide; it is also possible to use amphoteric compounds or anionic compounds.

Amongst the nonionic amphiphilic compounds, it is preferred to use:

1) the straight or branched polyglycerol ethers of the formulae, respectively

and

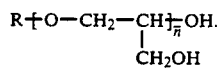

$\bar{n}$ representing an average statistical value from 1 to 6 (in a mixture) and R being a saturated or unsaturated, straight or branched aliphatic chain having 12 to 30 carbon atoms, a hydrocarbon radical of a lanolin alcohol or a 2-hydroxyalkyl radical of a long-chain α-diol;

2) polyoxyethylenated fatty alcohols and polyoxyethylenated sterols; 3) oxyethylenated or nonoxyethylenated polyol esters;

4) glycolipids of natural or synthetic origin, for example cerebrosides; and 5) ethers or esters of polyols containing two long-chain alkyl groups (having at least 8 carbon atoms) as the hydrophobic residue.

Various additives can be associated with the lipid compounds which are to form the small spheres; in order to modify the permeability or the surface charge of the said small spheres. In this respect, there may be mentioned the optional addition of long chain alcohols and diols, sterols, for example cholesterol, long chain amines and their quaternary ammonium derivatives, dihydroxyalkylamines, polyoxyethylenated fatty amines, long-chain aminoalcohol esters and salts and quaternary ammonium derivatives thereof, phosphoric acid esters of alcohols and in particular phosphoric acid esters of fatty alcohols, for example dicetyl phosphate, alkyl-sulphates, for example sodium cetyl-sulphate, and certain polymers such as polypeptides and proteins.

From 2 to 10% of lipids, relative to the total weight of the dispersion of small spheres to be mixed with the liquid phase L, are generally used to form the dispersion of small lipid spheres. In a preferred embodiment, the aqueous phases D and E are isoosmotic, and in the simplest embodiment, the aqueous phases D and E are identical.

At least one compound which is a hydrocarbon, halocarbon, polysiloxane, an ester of an organic or mineral acid, or an ether or polyether is advantageously chosen in order to form a liquid phase L. Hexadecane and paraffin oil may be mentioned amongst the hydrocarbons. Representative halocarbons include, for instance, perfluorodecahydronaphthalene and perfluorotributylamine.

According to an advantageous embodiment, the liquid phase L is introduced into the dispersion of small spheres in an amount from 2 to 70% by weight, relative to the weight of the dispersion of small spheres. It is preferred to introduce the liquid phase L into the dispersion of small spheres in an amount from, say, 20 to 2,000%, relative to the weight of amphiphilic substance(s) contained in the dispersion of small spheres.

The present invention also provides the stable dispersions obtained by the process of this invention. The field of application of these dispersions is very broad because it combines the field of emulsions of different types with dispersions of small spheres of ionic or nonionic lipids. The small lipid spheres can be used to encapsulate, between their concentric lipid laminae, layers of aqueous phase containing water-soluble active substances; furthermore, the lipid layers of the small spheres can contain active organic substances. Amongst the water-soluble active substances, there may be mentioned organic or inorganic compounds having a biological, microbiocidal, fungicidal, insecticidal, vitamin or photosensitive activity, medicaments, chemical reagents, catalysts, dyestuffs, complexing agents and gases ($O_2$ or $CO_2$). Amongst the liposoluble active substances, there may be mentioned antibiotics and antioxidants.

In the dispersions according to the invention, the presence of the droplets of liquid phase L constitutes an additional advantage because the droplets can contain substances soluble in an organic medium, the activity of which can be identical to or different from that of the substances trapped in the small spheres, the difference between the two groups of substances resulting essentially from opposite solubilities. By virtue of its function as solvent or vehicle, the liquid phase L itself can make it possible to bring an active substance to an application site; by way of example, perfluorinated compounds are transporters of oxygen and carbon dioxide, which makes it possible to envisage their use as blood substitutes. In certain cases, the liquid phase L can act as a lubricant, spreading agent, cleaning agent or polishing agent. If its molecular weight is relatively low, the volatility of the liquid phase L is such that it disappears after deposition; this can be very advantageous in surface-treatment processes or surface-coating processes. The liquid phase L can also contain a polymer, an oligomer, a prepolymer or a monomer; it can also contain fillers or additives such as dyestuffs, opacifiers or gelling agents.

The continuous aqueous phase of the dispersion according to the invention can itself contain dissolved substances similar to or different from the substances contained in the aqueous or lipid layers of the small spheres and in the liquid phase L.

It is to be understood that the small spheres behave as a first type of micro-reservoir, which slowly releases the trapped water-soluble and liposoluble substances. Furthermore, the droplets of liquid phase L constitute a second type of micro-reservoir, in which the dissolved compounds can be exchanged with an organic substrate, which may be that of a living being. The actions of the small spheres and liquid phase L can combine, complement one another or give rise to synergism. For example, the release of the active substances contained in the small spheres can be accelerated by the combined action of the temperature and the solvent power of the liquid phase L; this can be useful for carrying out a monomer polymerization operation or a crosslinking operation.

The following Examples further illustrate the present invention.

EXAMPLE 1

First step: Preparation of the dispersion of small spheres 4.275 g of a product of the general formula:

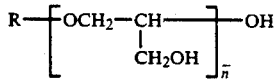

in which formula R is a hexadecyl radical and $\bar{n}$ has an average statistical value of 3, 4.275 g of cholesterol and 0.45 g of dicetyl phosphate are weighed into a stainless steel pot.

This mixture is heated to a temperature of about 110° C. until a clear liquid lipid phase is obtained, and this is then cooled to a temperature of 90° C. 22.5 g of a 0.5 M aqueous solution of glucose are added. The mixture is stirred gently with a spatula until an apparently homogeneous phase is obtained.

This is cooled to a temperature of 70° C. and 68.5 g of the same 0.5 M aqueous solution of glucose are added. The whole is agitated for 10 minutes by means of an T-MILA ultra-disperser, model CX 1020, rotating at 25,000 rpm. It is then cooled to 40° C.

Second step: Introduction of the water-immiscible liquid phase L 12.5 g of perfluorodecahydronaphthalene are added to 100 g of the dispersion of small spheres obtained in the first stage. This mixture is agitated for 5 minutes by means of the same ultra-disperser as that used at the end of the first stage of the present example.

This gives a stable dispersion in which the small spheres have an average size of less than 1 micron and in which the droplets have an average size of less than 1 micron. This dispersion can be used as a blood substitute.

In order to study the characteristics of this dispersion, the amount of glucose encapsulated by the small spheres, which are used as a perfluorodecahydronaphthalene stabilizer, is determined. For this purpose, the swelling S of the lipids constituting the small spheres is determined. If the weight of aqueous solution of glucose encapsulated is designated by WS and the weight of lipids is designated by WL, the swelling S is calculated by the formula:

$$S = \frac{WS}{WS + WL}$$

To carry out this determination, given that the weight of lipids WL used is known, it is necessary to determine the weight WS. 5 g of the final product are placed in a collodion dialysis bag, and this is dialyzed against 200 g of a 1.5% strength aqueous solution of sodium chloride (isoosmotic), whilst stirring. The amount of glucose not encapsulated by the vesicles is determined in the external saline medium after the dialysis equilibrium time (24 hours). The amount of glucose encapsulated, WS, is deduced therefrom and it is calculated that S=86%.

By way of comparison, the swelling of the small spheres before they are used as an oil stabilizer is determined by dialyzing 5 g of the dispersion obtained at the end of the first stage of this example against 200 g of an isoosmotic solution of sodium chloride. The Swelling S is found to be 87%.

EXAMPLE 2

First step: Preparation of the dispersion of small spheres

In a glass flask, 6.75 g of soya lecithin marketed under the name "Epikuron 200" by "Lukas Meyer", 1.8 g of cholesterol and 0.45 g of dicetyl phosphate are dissolved in 20 ml of chloroform.

This solution is lyophilized with the aid of a Virtis apparatus, model 1020. 91 g of a 1 M aqueous solution of glucose are added to the anhydrous lipid mixture obtained after lyophilization. This mixture is left to swell for 2 hours at a temperature of 40° C., under a nitrogen atmosphere. It is agitated for 10 minutes by means of the ultra-disperser defined in Example 1, and then cooled to ambient temperature. This gives a dispersion of small spheres.

Second step: Introduction of the water-immiscible liquid phase L 12.5 g of perfluorodecahydronaphthalene are added to 100 g of the dispersion of small spheres obtained in the first stage. This mixture is agitated for 5 minutes, at ambient temperature, by means of the ultra-disperser used in the first stage. This gives a liquid dispersion which contains small spheres having a diameter of less than 1 micron and perfluorodecahydronaphthalene droplets having an average diameter of less than 1 micron. This dispersion can be used as a blood substitute.

The swelling of the small spheres used to stabilize the perfluorodecahydronaphthalene was determined. The swelling S was found to be 74 %. The proportion of encapsulated glucose which escapes over 5 days is 36%. However, it was not possible directly to determine the swelling of the small spheres before dispersing the oil; in fact, it was found that, when dialyzed against 200 g of a 3% strength aqueous solution of sodium chloride (isoosmotic), the 5 g sample of the dispersion obtained at the end of the first stage deteriorated very rapidly; the small spheres lose their integrity and re-form a viscous phase which clogs the dialysis bag. It is thus apparent that, in this example, the perfluorodecahydronaphthalene droplets stabilize the small spheres obtained in the first stage. The swelling of the small spheres before dispersing the oil was determined by another method, at lower concentrations of lipids and glucose and after filtration on a column of gel; the swelling S is found to be 74%. The proportion of encapsulated glucose which escapes over 5 days is 45%. It is thus seen that the stability of the encapsulation is improved by the presence of the droplets of the water-immiscible liquid L.

The process used for the two-step preparation of the dispersions according to the invention, in the examples which now follow, is identical to that which has been described above in Examples 1 and 2, so that the examples which now follow only mention the products used and the corresponding amounts for each of the two steps of each example. The examples also mention, if appropriate, the swelling of the small spheres before and after dispersing the oil.

EXAMPLE 3

First step: Preparation of the dispersion of small spheres

The following products are used: Product of the general formula:

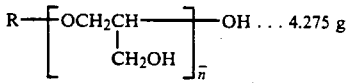

in which formula R is a hexadecyl radical and $\bar{n}$ has an average statistical value of 3;

| β-Sitosterol | 4.275 g |
|---|---|
| Dicetyl phosphate | 0.45 g |
| Glucose | 8.19 g |
| Water | 82.81 g |

This gives a dispersion of small spheres.

Second step: Introduction of the water-immiscible liquid phase L 12.5 g of a silicone oil marketed under the name "DOW 344" by "DOW CORNING" are added to the dispersion of small spheres obtained in the first step.

The swelling index of the small spheres before dispersing the silicone oil is 87%; the swelling of the small spheres after dispersing the silicone oil is 85%. The average diameter of the small spheres in the dispersion obtained is 1 micron; the average diameter of the droplets of silicone oil in the dispersion obtained is 2 microns.

The dispersion obtained can be used as an anti-foam agent.

EXAMPLE 4

First step: Preparation of the dispersion of small spheres

The following products are used: Product of the general formula:

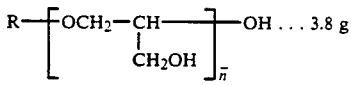

in which formula R is a hexadecyl radical and e,ovs/n/ has an average statistical value of 3;

| Cholesterol | 3.8 g |
|---|---|
| Dicetyl phosphate | 0.4 g |
| Cholesterol oleate | -0.8 g |
| Water | 91.2 g |

This gives a dispersion of small spheres.

Second step: Introduction of the water-immiscible liquid phase L 40 g of perfluorodecahydronaphthalene are added to 100 g of the dispersion of small spheres obtained in the first step. This gives a dispersion in which the small spheres have an average diameter of less than 1 micron and the perfluorodecahydronaphthalene droplets have an average diameter of less than 1 micron.

The dispersion thus obtained can be used as a blood substitute.

EXAMPLE 5

First step: Preparation of the dispersion of small spheres

The following products are used:

| Soya lecithin marketed under the name "Epikuron 145" by "Lukas Meyer" | 9 g |
|---|---|
| Distilled water | 91 g |

This gives a dispersion of small spheres.

Second step: Introduction of the water-immiscible liquid phase L 12.5 g of a hexadecane are added to 100 g of the dispersion of small spheres obtained in the first step. This gives a dispersion in which the small spheres have an average diameter of 0.5 micron and the hexadecane droplets have an average diameter of 2 microns. This dispersion can be used as a lubricant for textiles.

EXAMPLE 6

First step: Preparation of the dispersion of small spheres

The following products are used:

| Synthetic dipalmitoyl-lecithin | 8.5 g |
|---|---|
| Cholesterol | 1.0 g |
| Dicetyl phosphate | 0.5 g |
| Glucose | 0.1 g |
| NaCl | 0.054 g |
| KCl | 0.032 g |
| $MgCl_2$ | 0.007 g |
| $CaCl_2$ | 0.010 g |
| $NaH_2PO_4$ | 0.0096 g |
| $Na_2CO_3$ | q.s. pH 7.44 |
| Distilled water | q.s. 110 g |

This gives a dispersion of small spheres.

Second step: Introduction of the water-immiscible liquid phase L 30 g of perfluorotributylamine are added to 100 g of the dispersion of small spheres obtained in the first step.

This gives a dispersion according to the invention, in which the small spheres have an average diameter of less than 1 micron and the perfluorotributylamine droplets have an average diameter of less than 1 micron. A dispersion of this type can be used as a blood substitute.

EXAMPLE 7

First step: Preparation of the dispersion of small spheres

The following products are used:

| Sodium salt of N-(tallow fatty alkyl)-N-(dodecyl)-N-(N',N'-diethylaminoethyl)-asparagine (described in French Patent 1,397,231) | 4.95 g |
|---|---|
| Cholesterol | 3.6 g |
| Dicetyl phosphate | 0.45 g |
| Glucose | 8.19 g |
| Water | 82.81 g |

This gives a dispersion of small spheres.

Second step: Introduction of the water-immiscible liquid phase L 11 g of perfluorotributylamine are added to 100 g of the dispersion of small spheres obtained in the first step. The swelling of the small spheres before and after the second step is measured at 78%.

This gives a dispersion according to the invention, in which the small spheres have an average diameter of less than 1 micron and the perfluorotributylamine droplets have a diameter of less than 1 micron. A dispersion of this type can be used as a blood substitute.

EXAMPLE 8

First step: Preparation of the dispersion of small spheres

The following products are used:

| | |
|---|---|
| Dioctadecyl-dimethylammonium chloride | 3 g |
| Distilled water | 97 g |

This gives a dispersion of small spheres.

Second step: Introduction of the water-immiscible phase L 12.5 g of hexadecane are added to 100 g of the dispersion obtained in the first step. This gives a dispersion according to the invention, in which the small spheres have an average diameter of 1 micron and the hexadecane droplets have an average diameter of 2 microns.

This dispersion can be used as a lubricant for textiles.

EXAMPLE 9

First step: Preparation of the dispersion of small spheres

The following products are used:

| | |
|---|---|
| Oxyethylenated phytosterols with a statistical distribution having an average value of 5 ethylene oxide units (product marketed under the name "GENEROL 115 E5" by "HENKEL") | 6.75 g |
| Cholesterol | 2.25 g |
| Distilled water | 91.0 g |

This gives a dispersion of small spheres.

Second step: Introduction of the water-immiscible liquid phase L 25 g of paraffin oil are added to 100 g of the dispersion obtained in the first step. This gives a dispersion according to the invention, in which the small spheres have an average diameter of 0.5 micron and the paraffin oil droplets have an average diameter of 1 micron.

This dispersion can be used as an intestinal lubricant.

What is claimed is:

1. A process for the preparation of a stable dispersion comprising droplets of at least one water-immiscible liquid phase dispersed in a continuous aqueous phase, said aqueous phase having spheres dispersed therein whereby said droplets are stabilized in said dispersion by the presence therein of said spheres, said process comprising mixing by mechanical agitation said water-immiscible liquid phase with a dispersion of spheres in said continuous aqueous phase, said water-immiscible liquid phase consisting of a hydrocarbon, a halocarbon or polysiloxane, said spheres having an average diameter of 0.025 to 5 microns and consisting substantially of concentric lipid laminae encapsulating an aqueous phase between them, said lipid constituting said laminae consisting of (i) an ionic or nonionic amphiphilic substance capable of forming a lameller phase in said water and (ii) at least one additive so as to modify the permeability or surface charge of said spheres, and said continuous aqueous phase contains, as the only amphiphilic substance, the said ionic or nonionic amphiphilic substance constituting the laminae of said spheres, all said ionic or nonionic amphiphilic substances being enclosed in the laminae of said spheres.

2. The process of claim 1 wherein said additive is selected from a long chain alcohol or diol, a sterol, a long chain amine or quaternary ammonium derivative thereof, a dihydroxyalkylamine, a polyoxyethylenated fatty amine, a long chain aminoalcohol ester or a salt or quaternary ammonium derivative, thereof, a phosphoric acid ester of a fatty alcohol, an alkyl sulphate, a polypeptide or a protein.

* * * * *